United States Patent [19]

Lynch et al.

[11] Patent Number: 5,177,201
[45] Date of Patent: Jan. 5, 1993

[54] NITROGEN DEPROTECTED 4-ACYLOXYAZETIDIN-2-ONES

[75] Inventors: Joseph E. Lynch, Plainfield, N.J.; William L. Laswell, Perkasie, Pa.; Ralph P. Volante, East Windsor; Ichiro Shinkai, Westfield, both of N.J.

[73] Assignee: Merck & Co., Inc., Rahway, N.J.

[21] Appl. No.: 541,166

[22] Filed: Jun. 21, 1990

Related U.S. Application Data

[63] Continuation of Ser. No. 369,395, Jun. 21, 1989, abandoned.

[51] Int. Cl.$^5$ .................. C07D 407/04; C07D 205/08; C07B 41/14; C07F 7/18
[52] U.S. Cl. .................................... 540/200; 540/357; 549/491; 549/496
[58] Field of Search ........................................ 540/200

[56] References Cited

U.S. PATENT DOCUMENTS 4,260,618 4/1981 Christensen ......................... 540/360
4,791,207 12/1988 Salzmann et al. .................. 548/110

FOREIGN PATENT DOCUMENTS 0167155 1/1986 European Pat. Off. .

OTHER PUBLICATIONS

Andreoli, Chem Abs 106, 101679p (1986).
Ha, J. Amer. Chem. Soc. 106, 4819 (1984).
Stuart L. Schreiber et al., Tetrahedron Ltrs, vol. 24, No. 23, pp. 2363-2366 1983.
Bruce H. Lipshutz, Chem Rev. 1986, 86, 795-819.
Maria Altamura, et al., Syn Comm., 18(16&17), 2129-2133 (1988).
Derwent for JP-61-243079 (1985).
Klaus Gollnick, et al. Tetrahedron vol. 41, No. 11, pp. 2057 to 2068, 1985.
Masao Shiozaki, et al., Tetrahedron vol. 40, No. 10, pp. 1795 to 1802, 1984.
Paul J. Reider, et al., Tetrahedron Ltd, vol. 23, No. 22, pp. 2293-2296, 1982.
Curt Wentrup et al., J. Am. Chem. Soc. 1980, 102, 6161-6163.
Gunda I. Georg, et al. Tetrahedron Ltrs, vol. 26, No. 33, pp. 3903-3906, 1985.
Gunda I. Georg, et al., J. Am. Chem. Soc. 1987, 109, 1129-1136.

*Primary Examiner*—Mark L. Berch
*Attorney, Agent, or Firm*—Curtis C. Panzer; Ramymond M. Speer

[57] ABSTRACT

The 4-acyloxyazetidin-2-ones, which are intermediates in the production of carbapenems and penems, are produced from nitrogen deprotected 4-furanylazetidin-2-ones.

3 Claims, No Drawings

NITROGEN DEPROTECTED 4-ACYLOXYAZETIDIN-2-ONES

This is a continuation of application Ser. No. 369,395, filed Jun. 21, 1989, now abandoned.

The present invention relates to the preparation of 4-acyloxyazetidin-2-ones. More particularly, the present invention relates to the preparation of the above compounds through a nitrogen deprotected 4-furan-2-ylazetidin-2-one intermediate.

BACKGROUND OF THE INVENTION

Carbapenems and penems are well known antibiotics for treating a broad range of gram-negative and gram-positive bacterial infections.

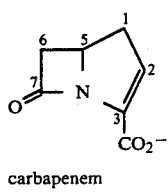

carbapenem

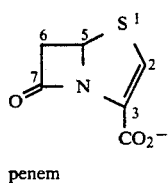

penem

Methods and intermediates for the manufacture of carbapenems and penems are thus matters of scientific and commercial importance.

One method for the production of carbapenems is described in GB 2,162,840, Cainelli, et al. As described therein, certain carbapenems are produced from 4-acetoxyazetidin-2-one intermediates.

These intermediates are in turn produced in a multi-step synthesis from 4-alkenylazetidin-2-one intermediates of the formula:

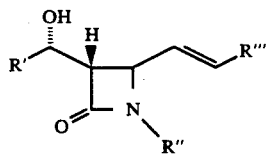

The starting materials to produce the 4-alkenylazetidin-2-one intermediates are:

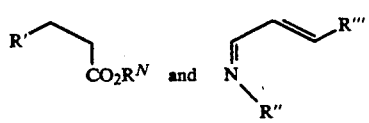

Thus, carbapenems may be produced through two principal intermediates from readily made or available starting materials. However, methods having fewer reaction steps to obtain the intermediates and improved yields are desirable.

Another method for the production of carbapenems is described in EPO 0167155, Kan, et al. Again, certain carbapenems are produced from 4-acetoxyazetidin-2-one intermediates. In this case however, these intermediates are in turn produced from 4-triorganosilyloxyazetidin-2-one intermediates of the formula:

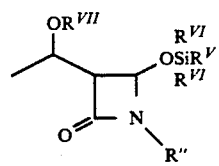

The starting materials to produce the 4-triorganosilyloxyazetidin-2-one intermediates are:

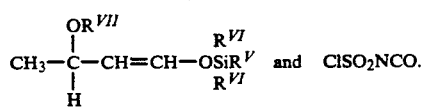

Thus, again, carbapenem may be produced through two principle intermediates from readily made or available starting materials. However, methods having fewer reaction steps to obtain the intermediates as well as methods using less hazardous starting materials than $ClSO_2NCO$ are desired.

A method for the production of penems is disclosed in Christensen, et al., U.S. Pat. No. 4,260,618 from 4-acetoxyazetidin-2-one intermediates. Herein, it is recommended that these intermediates be produced by cleaving penicillin which is produced by fermentation.

It is an object of the present invention to produce 4-acyloxyazetidin-2-one intermediates useful in the production of carbapenems from novel 4-furanylazetidin-2-ones.

It is a further object of the present invention to produce 4-acyloxyazetidin-2-one intermediates from starting materials which require no subsequent deprotection of nitrogen.

It is yet another object of the present invention to simplify the reactions required and improve the reaction yields in the production of 4-acyloxyazetidin-2-one intermediates by employing novel deprotected starting materials in novel processes.

It is still another object of the present invention to develop a method for the production of 4-acyloxyazetidin-2-one intermediates where an organic group is employed to protect the carbon in the 4-position of the azetidin-2-one and which subsequently may be converted to the 4-acyloxy substitution in the presence of unprotected nitrogen.

BRIEF DESCRIPTION OF THE INVENTION

Briefly, there is provided by the present invention a method for the production of 4-acyloxyazetidin-2-ones of the formula (I):

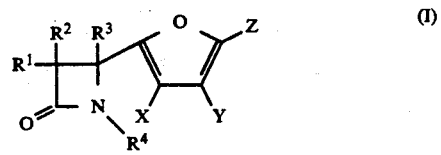

wherein $R^1$ and $R^2$ are independently selected from the group consisting of hydrogen, $C_{1-10}$ alkyl, $C_{1-10}$ fluoroalkyl, alpha-carbon substituted $C_{1-10}$ alkyl, alpha-carbon substituted $C_{1-10}$ fluoroalkyl, where the alpha-carbon substituent is selected from the group consisting of hydroxyl and protected hydroxyl; $R^3$ is selected from the group consisting of hydrogen and $C_{1-10}$ alkyl; $R^4$ is hydrogen; and X, Y and Z are independently selected from the group consisting of hydrogen, halogen, $C_{1-10}$ alkyl, $C_6$ or $C_{10}$ aryl, substituted $C_6$ or $C_{10}$ aryl, $C_{1-10}$ alkoxy, and $C_6$ or $C_{10}$ aryloxy.

DETAILED DESCRIPTION OF THE INVENTION

Herein, $R^1$ and $R^2$ represent those hydrogen, alkyl, and substituted alkyl substituents useful as 6-position substitution on carbapenems. $R^1$ and $R^2$ include, for example, hydrogen, methyl, ethyl, propyl, isopropyl, butyl, isobutyl, $HO-CH_2-$, $CH_3CH(OH)-$, $(CH_3)_2C(OH)-$, $(CH_2)_2C(OH)-$, $CH_3CH_2CH(OH)-$, $CH_3CH_2CH_2CH(OH)-$, $CH_3CH_2CH(CH_3)(OH)-$, $CH_3CH(CH_3)CH(OH)-$, $CF_3CH(OH)-$, $CHF_2CH(OH)-$, $FCH_2CH(OH)-$, $CH_3CHF-$, $F_2CH-$, $F_3C-$, $CH_3CF_2-$, etc.

In preferred embodiments, either $R^1$ or $R^2$ is hydrogen and, in a more preferred embodiment, $R^2$ is beta-hydrogen and $R^1$ is any of the above, excepting hydrogen, in an alpha orientation. Most preferably, $R^1$ is an alpha oriented 1-hydroxyethyl and $R^2$ is a beta oriented hydrogen.

The protected hydroxy is known in the antibiotic art and refers to a hydroxyl group protected by a suitable protecting radical rendering it inactive during chemical reaction. Of course the identity of this protecting radical will depend on the particular chemical reaction from which the hydroxyl group is being protected. A preferred protecting radical useful herein in the production of the desired 4-acyloxy-azetidin-2-one is dimethyl-t-butylsilyl (TBSDM). This protecting radical may suitable for subsequent reactions of the desired compound or may require replacement depending on the scheme selected to produce penen or carbapenem. Further protecting groups which might be employed include trimethylsilyl, benzyl, p-nitrobenzyl, p-nitrobenzyloxycarbonyl, diphenyl-t-butylsilyl, isopropyldimethylsilyl, phenyl, methyl, etc. Other protecting radicals for hydroxyl groups are known in the art (See T. W. Greene, *Protective Groups in Organic Synthesis*, John Wiley & Sons, Inc., 1981).

$R^3$ may be selected from hydrogen, methyl, ethyl, propyl, etc. Preferably, $R^3$ is hydrogen and has a beta orientation.

Suitable X, Y and Z are independently selected from any of hydrogen, methyl, ethyl, propyl, t-butyl, n-butyl, phenyl, p-chlorophenyl, hydroxy, methoxy, ethoxy, phenoxy, etc. Preferably, at least Z is hydrogen. More preferably, X, Y and Z are hydrogen. The principle consideration of selecting X, Y and Z is that they not interfere with the processes taught herein.

Flow sheets A and B depict a suggested synthesis for the starting material described in formula (I). Flow Sheet A depicts the manufacture of an imine. This imine of Flow Sheet A is reacted with a carboxyl derivative in Flow Sheet B to produce the 4-furan-2-ylazetidin-2-one starting material.

Referring to Flow Sheet A, an available or readily produced furfural 1 is condensed with an amine compound 2. In the case of such condensation, $R^4$ of compound 2 is not hydrogen. Preferably, of course, $R^4$ is a protecting radical for nitrogen and more preferably an organic aromatic protecting radical. Suitable as Compound 2 is benzylamine.

Referring to Flow Sheet B, compound 4 is a readily available or easily produced ester starting material having $R^1$ and $R^2$ substitution or precursors thereof. Suitable ester starting materials as compound 4 include methyl 3-hydroxypropanoate, methyl 3-hydroxypentanoate, methyl 3-hydroxy-4,4,4-trifluorobutanoate, methyl 3-fluorobutanoate, methyl 2-methyl-3-hydroxybutanoate, etc. Preferred is methyl 3-hydroxybutanoate. The nature of the ester group described as methyl is not critical and could be ethyl, propyl, etc.

As the first reaction step of Flow Sheet B, compound 4 is enolized by reaction with a base such as that prepared from n-butyllithium and diisopropylamine in tetrahydrofuran at about $-71°$ C. Subsequently and without isolation of the reaction product, the enolate is quenched by the addition of trimethyl-chlorosilane (ClTMS), again in tetrahydrofuran at about $-78°$ C., to produce a ketenesilylacetal, compound 5. In this reaction to produce compound 5, any unprotected hydroxy group on either $R^1$ or $R^2$ will be substituted with trimethylsilyl. This is a desirable result as a protecting group will later be necessary on any unprotected hydroxy of $R^1$ or $R^2$. If another type protecting group is desired, it should be added to the hydroxy of compound 4 prior to enolization. If another silyl protecting group is desired, then appropriate replacement should be made for trimethylchlorosilane in the reaction of quenching the enolate.

As the second reaction step of Flow Sheet B, the imine, compound 3, is added to ketenesilylacetal, compound 5 in dichloromethane at about $-20°$ C. in the presence of trimethylsilyltrifluoromethanesulfonate (TMSOTf). The resultant compound 6 contains $R^1$ through $R^3$ functionality, $R^4$ functionality restricted to protecting radical for nitrogen and the necessary functionality to close the azetidin-2-one ring. At this point or later in Flow Sheet B, the protecting radical for nitrogen, $R^4$, is converted to hydrogen. Preferably, the protecting group is removed from compound 6. For example, a benzyl protecting radical for nitrogen may be substituted with hydrogen through a hydrochloride by hydrogenation ($H_2/Pd/C$) in the presence of HCl and subsequent reaction with sodium hydroxide.

As the third reaction of Flow Sheet B, compound 6 is saponified to remove the methyl ester and produced compound 7. The saponification is carried out in water, raising the pH to high levels with sodium hydroxide.

Finally, starting material 8 is produced by dehydrating compound 7 to close the azetidin-2-one ring. The dehydration is carried out in 2-propanol with $NaHCO_3$ and methane sulfonylchloride MeS-Cl. A preferred starting material 8 contains an $R^1$ with hydroxy substitution. This hydroxy substitution should be protected as appropriate from reaction conditions in which the starting material 8 is to be employed. The most preferred starting material 8 is shown in Example 6 as compound E9.

Flow Sheets C and D depict processes whereby the novel starting material of formula I may be converted to 4-acyloxyazetidin-2-ones. Briefly, Flow Sheet C shows the singlet oxygen oxidation of 4-furanylazetidin-2-one to the desired 4-acyloxyazetidin-2-one. Flow Sheet D shows a variation of Flow Sheet C where a peroxide, ROOH, is present with the singlet oxygen.

Referring to Flow Sheet C, starting material 8 from Flow Sheet B is exposed to singlet oxygen which may be generated by contacting ground state oxygen with a photo-sensitizer which has been excited by irradiation with visible light at temperatures below about 0° C. The product of such exposure of starting material 8 is believed to be adducts 9 and 10 which have a fused peroxy ring on the 4-position furanyl. Without isolating adducts 9 and 10, a desired 4-acyloxy-azetidin-2-one 11 may be produced therefrom by simply warming to about room temperature i.e. about 0° C. to 50° C. The desired 4-acyloxyazetidin-2-one 11 may be easily converted to the most desired 4-acetoxy-azetidin-2-one 12 by transesterification using potassium acetate in water.

A number of methods are available for generating singlet oxygen, for example:

1) Visible light exposure of ground-state molecular oxygen in the presence of a photosensitizer such as chlorophyl, hematoporphyrin, Rose Bengal, eosin and the like, as described by A. Nickon and W. L. Mendelson, J. Am. Chem. Soc. 87, 3921 (1965) and K. Gollnick and G. O. Schenk, Pure and Applied Chem., 9,507 (1964), or as described in U.S. Pat. No. 3,281,415.

2) Electrodeless discharge of gaseous oxygen, as described by E. J. corey and W. C. Taylor, J. Am. Chem. Soc. 86, 3881 (1964).

3) Use of hypochlorites and hydrogen peroxide. This method is described by C. S. Foote and S. Wexler, J. Am. Chem. Soc. 86, 3879 and 3881 (1964), and in U.S. Pat. No. 3,274,181.

4) Use of the benzyl cyanide; hydrogen peroxide; base system, described by E. McKeown and W. A. Waters, Nature, 203, 1063 (1964).

5) Use of hydrogen peroxide and oxalyl chloride, as described by E. A. Chandross, Tetrahedron Letters, 12,761 (1963), and Corey, cited above.

6) Use of ozone and phosphines, phosphites, etc, as given by Q. E. Thompson, J. Am. Chem. Soc. 83,845 (1961) and Corey, cited above.

7) By the reaction of hydrogen peroxide in aqueous solution with Fe (II), (III), or Ce (IV) ions, described by Stauff and Lohman, Z. physikal Chem., N. F., 40, 123 (1964) and 8) By pyrolysis of aromatic endoperoxides, such as anthracene or tryptycene endoperoxide. The 9, 10-diarylanthracene endoperoxides are especially useful.

Of course, the method chosen should not produce by-products or have reagents that will undesirably react with the azetidinone intermediates or end-products. The preferred method generating singlet oxygen by visible light exposure of ground-state molecular oxygen in the presence of a photosensitizer.

In the preferred method, singlet oxygen is generated by contacting ground-state molecular oxygen with a suitable photosensitizer which is activated by irradiation with visible light in an appropriate organic solvent. The generation of the singlet oxygen and exposure of the starting material 8 to the singlet oxygen is carried out by bubbling oxygen through a solution containing photosensitizer, starting material 8, a light source and cooled to between −70° C. and 0° C. Suitable sensitizers are those organic compounds which have a large molar absorptivity in the visible part of the electromagnetic spectrum, a high quantum yield of triplet formation, a long triplet lifetime, a low tendency toward hydrogen abstraction and self-oxidation, and a triplet energy not far above the energy of singlet oxygen to permit efficient energy transfer to oxygen. Many common dyes meet these requirements adequately. Typical classes of dyes that can advantageously be used in the olefin oxidation process of this invention are the xanthenes (rose bengal, erythrosin, eosin, fluorescein), the thiasines (methylene blue), the porphyrins (chlorophyll a and b, hematoporphyrin), the porphins and the phthalocyanines and mixtures thereof. These and other dyes are disclosed in Denny, et al., in "Organic Reactions", vol. 20 (W. G. Dauben-editor-in-chief), published by John Wiley & Sons, pp. 133-136, incorporated herein byreference. A preferred dye sensitizer is methylene blue.

For optimum efficiency, the amount of photosensitizer should neither be very low nor very high. At very low concentrations the sensitizer may not absorb all the available useful light. At too high a concentration, it absorbs all the useful light within a short distance from its entrance to the solution and depletes oxygen in that region of the reaction vessel. Preferred amounts of sensitizer range from about 0.01% to about 2.5%, more preferably amounts range from about 0.05% to about 1.3%. Suitable organic solvents are preferably an alcohol, particularly the lower alkanols, e.g., methanol, ethanol, propanol, i-propanol, butanol, etc.

Any source of visible light is suitable for the activation of the sensitizer. However, for maximum efficiency, the source should strongly emit light of the wavelength corresponding with the absorptivity maximum of the sensitizer. Thus, a halogen lamp is suitable and a vapor discharge tube is particularly suitable for use herein.

Referring to Flow Sheet D, starting material 8 is exposed to singlet oxygen in the same manner as described in Flow Sheet C producing adducts 9 and 10. The difference herein with the exposure to singlet oxygen of Flow Sheet A is that there is also present in the solution a peroxide of the formula R'OOH which reacts with adducts 9 and 10 in situ to produce peroxide 13. Suitable R' are hydrogen or acyl of from 1 to 6 carbon atoms, for example, acetyl, propionyl, n-butyryl, isobutyryl, etc. Preferred R' are hydrogen and acetyl.

From peroxide 13 the reaction scheme to the desired 4-acyloxyazetidin-2-one differs depending on the nature of R'. Where R' is acyl, simply warming peroxide 13 from the sub-zero temperatures of exposure to singlet oxygen will rearrange and cleave the 4-furanyl substitution to 4-acyloxy. Where R' is hydrogen, peroxide 13 is treated with an organic acid anhydride in an organic solvent at about 0° C. to produce acylated compound 14. Suitable organic acid anhydrides include acetic acid anhydride, propionic acid anhydride, n-butyric acid anhydride, etc. Acylated compound 14 will rearrange and cleave the 4-furanyl substitution to 4-acyloxy upon warming from the 0° C. temperature of acylation.

Additional process to employ the nitrogen deprotected compound of formula 1 are found in U.S. Pat. No. 5,104,800 and U.S. Pat. No. 4,923,982. Each of these applications disclosed processes by which compounds of formula 1 are converted to 4-acyloxyazetidin-2-ones.

Flow Sheet A

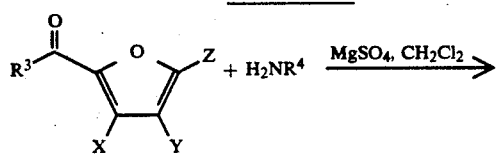

1      2

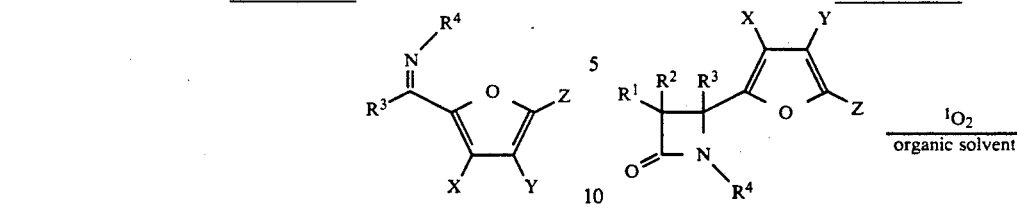
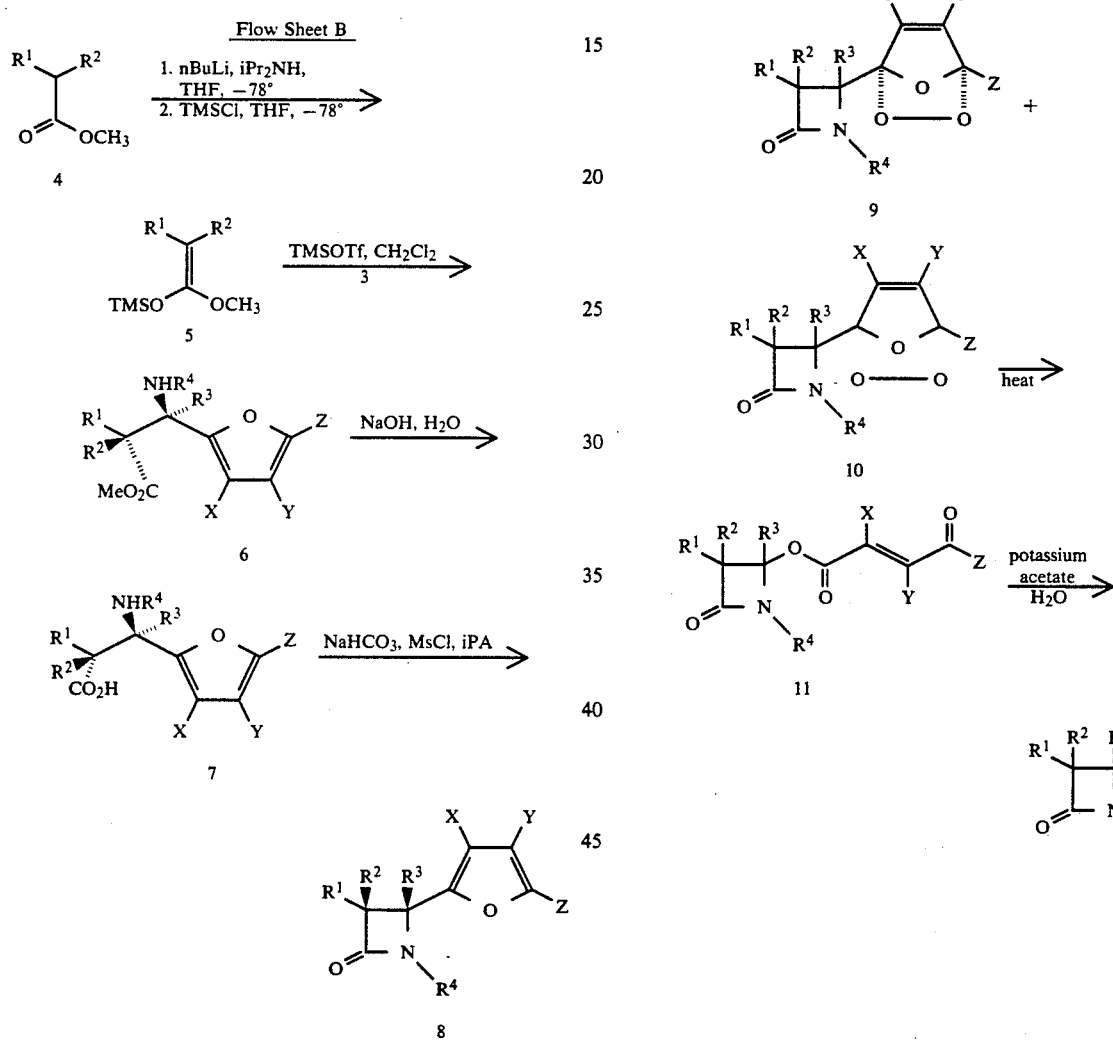
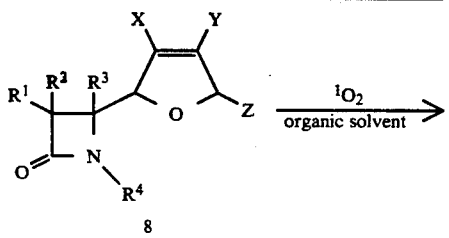

Flow Sheet D

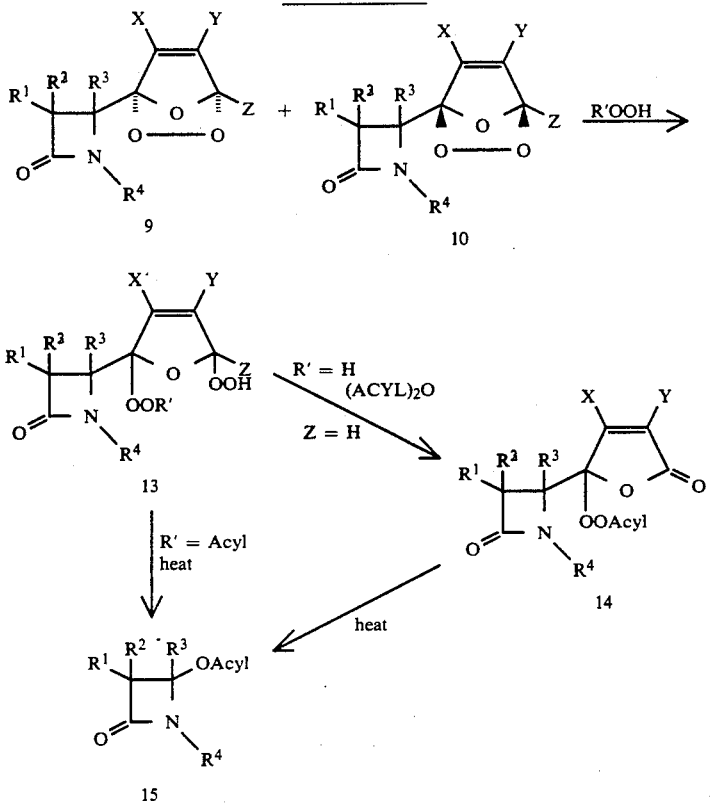

Any of compounds 11, 12 or 15 may be employed to make carbapenems or penems by well known methods. For example, 6-(1'-hydroxyethyl)-2-substituted-pen-2-em-3-carboxylic acid may be made from the above compounds as described in U.S. Pat. No. 4,260,618 hereby incorporated by reference. Therein, a 4-acyloxyazetidin-2-one is reacted with a substituted 1-thienoacetate derivative to provide a seco-lactam. Halogenation of the seco-lactam producer a compound which can be cylized by treatment with a strong base to the penem. Further use of compounds 11, 12 and 15 to produce carbapenems are taught in Salzman, T. N., et al., J. Am. Chem. Soc., 1980, 102, 6161 and Reider, P. J., et al., Tetrahedron Lett., 1982, 23, 379.

The following examples are illustrative of the best mode of carrying out the instant invention as contemplated by us and should not be construed to be limitations on the spirit or scope of the instant invention.

EXAMPLE 1

(3R)-Z-1-Methoxy-1,3-bis-trimethylsilyloxy-1-butene

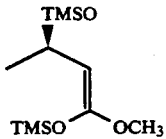   E2

1.54M nBuLi (237 mL, 0.365 mol) was added to diisopropylamine (41.15 g, 0.407 mol) in dry THF (740 ml) at −78° C. under $N_2$. (R) Methyl 3-hydroxybutanoate, E1, (20.00 g, 0.169 mol) in THF (340 mL) was added dropwise such that the temperature did not rise above −71° C. After a 30 minute age chlorotrimethylsilane (40.5 g, 0.373 mol) in THF (100 mL) was added so as to maintain the temperature below −71° C. The solution was stirred at −78° C. for 2 hours, warmed to 0° C. and concentrated in vacuo. Hexane (500 mL) was added and the mixture concentrated again. A second portion of hexane (500 mL) was added and the mixture was filtered and concentrated to a pale yellow oil (40.76 g). Distillation gave silyl ketene, E2, as a clear colorless oil b.p. 75°-80° C./0.25 mm (30.32 g, 79%).

EXAMPLE 2

(2S,3R,1″R)-Methyl-2-(1'-N-benzylamino-1'-(furan-2″-yl))-3-hydroxybutyrate

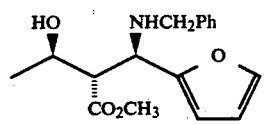   E5

Furfural E3 (4.98 g, 51.8 mmol) was added to benzylamine E4 (5.55 g, 51.8 mmol) in $CH_2Cl_2$ (25 mL). $MgSO_4$ (5 g) was added and the mixture was stirred for 2 hours, filtered and concentrated. The crude oil was redissolved in dry $CH_2Cl_2$ (60 mL) and concentrated repeatedly (2×) until the solution was dry (<10 mg $H_2O$/L). Trimethylsilyl trifluoromethanesulfonate (1.15 g, 5.18 mmol) was added to the imine above in $CH_2Cl_2$ (60 mL) at −20° C., after 5 minutes ketenesilylacetal, E2, (13.6 g, 51.8 mmol) was added and the solution aged for 18 hours. A second portion of ketenesilylacetal, E2, (3.6 g, 13.7 mmol) was added and the solution aged 16 hours. After warming to room temperature the solution was concentrated and redissolved in ethyl acetate (100 mL). The ethyl acetate solution was extracted with 2N HCl (50 mL); the aqueous solution was then treated with 5N NH4OH to give a pH>9 and was extracted with CH2Cl2 (50 mL). The CH2Cl2 solution was dried (MgSO4) and concentrated to give amino ester, E5, as a yellow oil 13.7 g, 87.7%.

EXAMPLE 3

(2S,3R,1"R)-Methyl-2-(1'-amino-1'-(furan-2"-yl))-3-hydroxybutyrate Hydrochloride

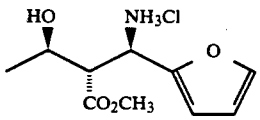
E6

12N HCl (0.48 mL, 5.76 mmol) and 10% Pd/C (170 mg) were added to the amino ester, E5, (1.75 g, 5.76 mmol) in methanol (17 mL). The mixture was hydrogenated at 1 psig $H_2$ at 25° C. until 98% of the starting material had been consumed (HPLC 1:1 $CH_3CN:H_2O$ (0.1% $H_3PO_4$), C8 column, 3 mL/min). The solution was filtered and concentrated to a white solid which was dissolved in 2-propanol (7 mL). Ethylether (30 mL) was then added dropwise with stirring to give hydrochloride, E6, as white needles which were collected on a filter, washed with 4:1 ether:2-propanol (2×5 mL) and dried in vacuo (1.21 g, 79.5%).

EXAMPLE 4

(2S,3R,1"R)-2-(1'-Amino-1'-(furan-2"-yl))-3-hydroxybutyric acid

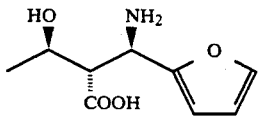
E7

The amino ester hydrochloride, E6, (55.69 g, 0.223 mol) was dissolved in $H_2O$ (225 mL). 5N NaOH was added to pH=12.5; the pH was maintained at pH 12.5 with a pH controller for 18 hours. The solution was then acidified to pH 2 and loaded onto a column of Dowex 50W X 2 resin (700 mL). The column was washed with $H_2O$ (1400 mL) then eluted with 1.5N NH4OH. The fractions containing the amino acid were concentrated in vacuo to a white solid. 2-Propanol (400 mL) was added and the mixture was concentrated to dryness. The resulting solid was stirred in 2-propanol (400 mL) for 16 hours, collected on a filter, and then dried in vacuo to give amino acid, E7, as an off-white solid (40.99 g, 92.2%).

EXAMPLE 5

(1"R,3S,4R)-3-(1"-Hydroxyethyl)-4-(furan-2'-yl)-azetidin-2-one

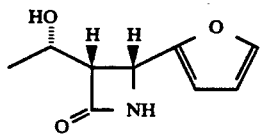

NaHCO3 (207.7 g, 2.47 mol) and then methanesulfonyl chloride (59.05 g, 0.51 mol) were added to dry 2-propanol (10.3 L). The amino acid E7 (40.99 g, 0.206 mol) was added and the mixture was stirred at 25° C. under $N_2$ for 39 hours. The mixture was concentrated, and the resulting solid triturated in ethyl acetate (2.5 L). The mixture was filtered and concentrated to a yellow oil (60 g). The oil was dissolved in ethyl acetate (100 mL), stirred with charcoal (3.5 g), filtered and concentrated to 120 ml. Hexane was added to the cloud point and the solution was seeded, hexane (total of 45 mL) was added dropwise. The mixture was stirred at ambient temperature for 1 hour., filtered and the solid was washed with 1:1 hexane:ethyl acetate (2×15 mL) and dried (13.17 g, 35%). The mother liquor was filtered through a short column of silica gel eluting first with 1:1 hexane:ethyl acetate (500 mL) then 1:2 hexane:ethyl acetate (500 mL); the fractions containing the azetidinone were concentrated to an oil that solidified on standing. The solid was broken-up and slurried in 1:1 hexane:ethyl acetate (30 mL), filtered, washed with the same solvent, (10 mL) and dried to give the desired azetidinone, E8, (11.31 g, 31%), total yield 66%.

EXAMPLE 6

(1"R,3S,4R)-2-S(1"-t-Butyldimethylsilyloxyethyl)-4-(furan-2'-yl-azetidin-2-one

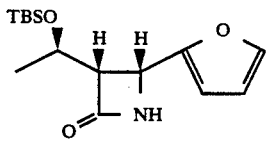
E9

Imidazole (5.63 g, 82.7 mmol) was added to 4-(furan-2-yl)-3-(1-hydroxyethyl)azetidin-2-one, E8, (10.00 g, 55.16 mmol) in dry DMF (25 mL). After cooling to 0° C., t-butyldimethylsilyl chloride (9.14 g, 60.67 mmol) was added, the cooling bath was removed and the solution was stirred at ambient temperature for 18 hours. Hexane:ethylacetate (1:1 75 mL) and water (50 mL) were added; the organic layer was washed with water (2×50 mL), dried (Mg SO4), and concentrated to give the silyloxy azetidinone, E9, as a yellow oil (16.08 g, 98.6%).

EXAMPLE 7

(1"R,3R,4R)-3-(1"-t-Butyldimethylsilyoxy)-4-(3'-formyl-prop-2'-ene-1'-yl)-azetidin-2-one

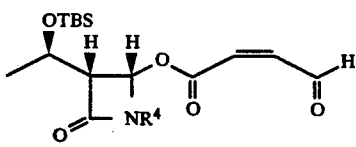
E10

Oxygen was bubbled through a solution of the furanylazetidinone, E9, (591 mg) and methylene blue chloride (5 mg) in acetone (10 mL) at −30° C. while irradiating with a 400 W halogen lamp for 2 hours. The solution was warmed to ambient temperature (22°–24° C.) and aged for 20 minutes. Concentration in vacuo and chromatography on silica gel gave the desired azetidinone, E10, as an oil (62 mg, 10%).

EXAMPLE 8

(1″R,3R,4R)-3-(1‴-t-Butyldimethylsilyoxyethyl)-4-acetoxyazetidin-2-one

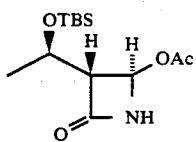   E11

Oxygen was bubbled through a solution of the furanylazetidinone, E9, (591 mg) and methylene blue chloride (5 mg) in acetone (10 mL) at −30° C. while irradiating with a 400 W halogen lamp for 2 hours. The solution was warmed to ambient temperature and after a 20 minute age, potassium acetate (anhydrous, 1 g) was added. The mixture was stirred for 5 hours and ether (20 ml) and water (10 mL) were added. The resulting emulsion was broken up by addition of saturated sodium chloride solution (5 mL), the organic layer was concentrated and chromatographed on silica gel (2:1 hexane:ethyl acetate) giving the acetoxy azetidinone, E11, as a white solid (134 mg, 23%).

EXAMPLE 9

(1″R,3R,4R)-3-(1‴-t-butyldimethylsilyloxyethyl)-4-acetoxyazetidin-2-one E11 and
(1″R,3R,4S)-3-(1‴-t-butyldimethylsilyloxyethyl)-4-acetoxyazetidin-2-one.

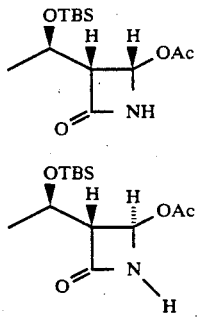

Oxygen was bubbled into a solution of the furanylazetidinone, E9, (295.6 mg, 1.00 mmol) and methylene blue chloride (5 mg) in acetone (3 mL) and 30% $H_2O_2$ (1 mL) at −20° C. which was irradiated with a 400 W halogen lamp for 2 hours. The solution was warmed to 0° C., diluted with ether (20 mL), washed with water (3×10 mL), dried (MgSO$_4$), and concentrated to 5 mL. Methylene chloride (30 mL) was added and the solution was concentrated to 5 mL. The solution was cooled to 0° C., acetic anhydride (0.3 mL) and pyridine (0.28 mL) were added and the solution was allowed to stand at 0° C. for 16 hours. Hexane (7 mL) was added and the solution was washed with 2N HCl (2 mL) then 3% NaHCO$_3$ (5 mL), dried (MgSO$_4$), and concentrated to a brown foam (368.5 mg). Acetonitrile (3 mL) was added and the solution was heated at 50° C. for 4 hours, concentrated and chromatographed on silica gel (2:1 hexane:ethyl acetate) giving the acetoxyazetidinone, E11, and E12 in a 3:4 ratio (64 mg, 22%).

What is claimed is:

1. A starting material for the production of 4-acyloxyazetidin-2-ones, said starting material of the formula:

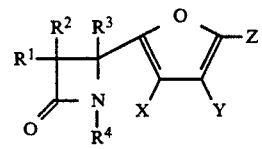

wherein $R^1$ and $R^2$ are independently selected from the group consisting of hydrogen, alpha-carbon substituted $C_{1-10}$ alkyl, and alpha-carbon substituted $C_{1-10}$ fluoroalkyl, where the alpha-carbon substituent is selected from the group consisting of hydroxyl and silyl protected hydroxyl and where $R^2$ is beta hydrogen and $R^1$ is other than hydrogen, $R^3$ is selected from the group consisting of hydrogen and $C_{1-10}$ alkyl; $R^4$ is hydrogen; and X, Y and Z are independently selected from the group consisting of hydrogen, halogen, $C_{1-10}$ alkyl, $C_6$ or $_{10}$ aryl, $C_{1-10}$ alkoxy, and $C_6$ or $_{10}$ aryloxy.

2. The compound of claim 1 wherein $R^2$ is beta-hydrogen and $R^1$ is alpha oriented 1-hydroxyethyl.

3. The compound of claim 1 wherein X, Y and Z are hydrogen.

* * * * *